(12) United States Patent
Schwarzentruber et al.

(10) Patent No.: US 9,579,291 B2
(45) Date of Patent: Feb. 28, 2017

(54) COATED CONTROLLED RELEASE ACTIVE AGENT CARRIERS

(71) Applicant: OMYA DEVELOPMENT AG, Oftringen (CH)

(72) Inventors: Patrick Schwarzentruber, Habsburg (CH); Nicola Di Maiuta, Zuchwil (CH); Joachim Schoelkopf, Killwangen (CH); Catherine Jean Ridgway, Mühlethal (CH); Patrick A. C. Gane, Rothrist (CH)

(73) Assignee: Omya International AG, Oftringen (CH)

( * ) Notice: Subject to any disclaimer, the term of this patent is extended or adjusted under 35 U.S.C. 154(b) by 0 days.

(21) Appl. No.: 14/349,850

(22) PCT Filed: Nov. 8, 2012

(86) PCT No.: PCT/EP2012/072161
§ 371 (c)(1),
(2) Date: Apr. 4, 2014

(87) PCT Pub. No.: WO2013/068478
PCT Pub. Date: May 16, 2013

(65) Prior Publication Data
US 2014/0248340 A1   Sep. 4, 2014

Related U.S. Application Data

(60) Provisional application No. 61/559,253, filed on Nov. 14, 2011.

(30) Foreign Application Priority Data

Nov. 10, 2011 (EP) .................................. 11188597

(51) Int. Cl.
*A61K 33/10* (2006.01)
*A01N 25/34* (2006.01)
(Continued)

(52) U.S. Cl.
CPC .............. *A61K 9/4816* (2013.01); *A01N 25/28* (2013.01); *A61K 9/2866* (2013.01);
(Continued)

(58) Field of Classification Search
None
See application file for complete search history.

(56) References Cited

U.S. PATENT DOCUMENTS 4,657,784 A     4/1987   Olson
5,631,296 A *   5/1997   Birrenbach et al. .......... 514/570
(Continued)

FOREIGN PATENT DOCUMENTS

EP     1974807 A1   10/2008
EP     2070991 A1    6/2009
(Continued)

OTHER PUBLICATIONS

Hahn et al.; Environmental Health (2010); 9:7; 11 pages.*
(Continued)

*Primary Examiner* — Jeffrey T Palenik
(74) *Attorney, Agent, or Firm* — Amster, Rothstein & Ebenstein LLP (57) ABSTRACT

The present invention relates to carriers for the controlled release of active agents, comprising a core, comprising surface reacted natural or synthetic calcium carbonate, and at least one active agent, wherein said at least one active agent is associated with said natural or synthetic surface-reacted calcium carbonate, and wherein said surface-reacted natural or synthetic calcium carbonate is a reaction product of natural or synthetic calcium carbonate with carbon diox-
(Continued)

ide and one or more acids, wherein the carbon dioxide is formed in situ by the acid treatment and/or is supplied from an external source, and a coating encapsulating the core. It furthermore relates to the preparation of loaded carriers, as well as their use in different applications.

25 Claims, 4 Drawing Sheets

(51) Int. Cl.
    *A61K 9/48*     (2006.01)
    *A61K 9/20*     (2006.01)
    *A61K 9/28*     (2006.01)
    *A61K 9/14*     (2006.01)
    *B05D 3/10*     (2006.01)
    *A61K 47/00*     (2006.01)
    *A61K 31/425*     (2006.01)
    *A61K 9/50*     (2006.01)
    *A01N 25/28*     (2006.01)

(52) U.S. Cl.
    CPC .......... *A61K 9/4833* (2013.01); *A61K 9/5078* (2013.01); *A61K 31/425* (2013.01); *A61K 9/5047* (2013.01)

(56) References Cited

U.S. PATENT DOCUMENTS

| | | |
|---|---|---|
| 5,958,458 A | 9/1999 | Norling et al. |
| 2004/0020410 A1 | 2/2004 | Gane et al. |
| 2009/0280172 A1 | 11/2009 | Carreno-Gomez |

FOREIGN PATENT DOCUMENTS

| | | |
|---|---|---|
| EP | 2168572 A1 | 3/2010 |
| EP | 2264108 A1 | 12/2010 |
| EP | 2264109 A1 | 12/2010 |
| GB | 1409468 | 10/1975 |
| WO | 0039222 A1 | 7/2000 |
| WO | 2004083316 A1 | 9/2004 |
| WO | 2005121257 A2 | 12/2005 |
| WO | 2009074492 A1 | 6/2009 |
| WO | 2010121619 A1 | 10/2010 |
| WO | 2010121620 A1 | 10/2010 |

OTHER PUBLICATIONS

Official Journal of the European Communities; "Directive 98/8/EC of the European Parliament and of the Council of Feb. 16, 1998" (1998); 63 page pdf.*
International Search Report dated Dec. 5, 2012 for PCT Application No. PCT/EP/2012/072161.
Written Opinion of the International Searching Authority dated Dec. 5, 2012 for PCT Application No. PCT/EP/2012/072161.

* cited by examiner

COATED CONTROLLED RELEASE ACTIVE AGENT CARRIERS

CROSS-REFERENCE TO RELATED APPLICATIONS

This application is a U.S. national phase of PCT Application No. PCT/EP2012/072161, filed Nov. 8, 2012, which claims priority to European Application No. 11188597.6, filed Nov. 10, 2011 and U.S. Provisional Application No. 61/559,253, filed Nov. 14, 2011.

The present invention relates to new coated controlled release active agent carriers, a method for their production, and their uses.

Controlled release formulations are generally known in the art, especially with respect to pharmaceutical formulations. Such preparations are e.g. formulated to dissolve slowly and release a drug over time in order to prolong the effectiveness of the active. Sustained-release tablets are often formulated so that the active ingredient is typically embedded in a matrix of insoluble substance, such as e.g. polyacrylic acids, so that the dissolving active has to find its way out through the holes in the matrix.

Alternatively, it is known to apply a coating providing controlled release on an otherwise immediate release formulation. Such coatings are typically selected from polymeric substances. A typical example therefore are formulations for the oral administration being coated with an acid resistant, but alkali soluble coating, in order to ensure the passage through the stomach without loss of the active agent, and the subsequent release of the agent in the alkaline intestinal environment, or to prevent loss of the pharmaceutical agent during processing, as well as delaying release of the pharmaceutically active substance beyond the disintegration of a rapidly disintegrating dosage form, e.g. in the mouth, as described in US 2009/0280172 A1.

In this respect, the direct coating of active agents often has considerable disadvantages. Thus, it can be taken from GB 1,409,468 that when fine particles are coated, the individual particles adhere to one another and form larger agglomerates during coating, which cannot be avoided even by coating the particles in a fluidised bed or by applying dilute coating solutions, wherein known encapsulation techniques impose astringent requirements upon the stability of the substance to be coated as there is a danger of degradation reactions during the process in the event of incompatibility between solvent and substance, or a danger of losses of the substance due to its solubility in the solvent.

According to GB 1,409,468, this problem is solved by a particular choice of the solvent, in which the coating substance is dissolved.

Controlled release formulations are useful in pharmaceutical applications, but are also interesting in other fields, such as in paper, paint coating, agricultural, biological, cosmetic or any other technical applications, where it is important that the active agent is released at a specific target environment and is not released unless this environment is reached, or a prolonged release over a certain time is desired.

For example, controlled release formulations are also used for avoiding that mixtures of active agents react with each other before their application, wherein conventional coatings often fail to protect the corresponding active agent as can be taken from U.S. Pat. No. 4,657,784 describing high efficiency encapsulation of bleach particles by applying several layers of coatings with different melting points and heat treating the encapsulated particles.

Controlled release, thus, can mean immediate release under certain conditions, e.g. depending on the temperature, pH or the milieu at the target environment.

In any applications, useful controlled release formulation should meet the following requirements:
 (i) retention of a sufficient quantity of active agent prior to the release at the target environment
 (ii) release of a sufficient quantity of active agent at the target environment, and
 (iii) sufficient protection by the carrier prior to delivery and release at the target environment so that it remains sufficiently active.

Meeting the above requirements is a demanding problem, wherein the controlled release formulation has to be selected depending on the nature of the active agent to be transported and the environment, in which the active agent has to be released, or, possibly has to be protected until the target environment is reached.

Thus, there is a continuous need for new and improved carriers.

For example, carriers for the controlled release of heat-sensitive agents degrading at certain temperatures, not only should protect the active agent from detrimental temperatures until the target environment is reached, or before the release is completed, but also should release the active agent at temperatures being low enough not to cause degradation.

Thus, improved controlled release formulations not only should generally provide controlled release of the active agent, but also reliably transport the active agent to the target environment even under conditions being harmful to the active agent or to conventional coating material, and should be easily available and processed.

For example, WO 2010/121619 A1 and WO 2010/121620 A1 mention chewing gums comprising particulate material for the controlled release of active ingredients, the particulate material comprising a combination of one or more active ingredients, and an inorganic mineral filler, wherein the active ingredient is reversibly absorbed into and/or adsorbed onto the inorganic mineral filler, and wherein the BET specific surface area of the inorganic mineral filler is above 15 $m^2/g$. However no mention is made as to a method or further components to improve protection of the active ingredients, or improve or control the release characteristics of the carrier. To the contrary, the release of active ingredients essentially is effected by chewing, i.e. mechanically, and not due to a specific composition.

Carriers providing excellent controlled release properties are e.g. known from EP 2 168 572, and are based on surface-reacted calcium carbonate. It has turned out that the use of surface reacted calcium carbonate as a carrier for active agents is beneficial, e.g. for applications where a high load sustained "slow-release effect" is needed. In this respect, the porous structure of the surface-reacted calcium carbonate is predestined for a significant uptake of polar as well as non-polar fluids.

Thus, the porous structure of surface-reacted calcium carbonate provides a high load extended release effect in contrast to "standard" ground calcium carbonate (GCC), which even in pellet form provides only a low load release. This is essentially due to the intra-particle pore volume of the surface-reacted calcium carbonate being much bigger than the inter-particle volume of GCC only.

It has now been found that the surface-reacted calcium carbonate particles according to EP 2 168 572 not only provide excellent controlled release properties, but also have a thermal insulation effect, which can even be improved by encapsulating the surface-reacted calcium carbonate based carriers.

It has furthermore turned out that the encapsulation of said surface-reacted calcium carbonate carriers by means of a coating covering the surface of said carrier significantly improves the protection characteristics of the carrier with respect to the active agent to be released, and allows for an even more precise control of the active agent release depending on the environmental conditions.

Thus, according to the present invention, the above problem has been solved by a carrier for the controlled release of active agents, comprising:

a core, comprising
surface-reacted natural or synthetic calcium carbonate, and
at least one active agent,
wherein said at least one active agent is associated with said natural or synthetic surface-reacted calcium carbonate, and wherein said surface-reacted natural or synthetic calcium carbonate is a reaction product of natural or synthetic calcium carbonate with carbon dioxide and one or more acids, wherein the carbon dioxide is formed in situ by the acid treatment and/or is supplied from an external source, and
a coating encapsulating the core.

The core of the carrier according to the present invention comprises surface-reacted natural or synthetic calcium carbonate, wherein preferred synthetic calcium carbonate is precipitated calcium carbonate (PCC) selected from the group comprising aragonitic, vateritic or calcitic mineralogical crystal forms or mixtures thereof.

The natural calcium carbonate is preferably selected from calcium carbonate containing minerals selected from the group comprising marble, chalk, calcite, dolomite, limestone and mixtures thereof.

In a preferred embodiment, the natural or synthetic calcium carbonate is ground prior to the treatment with one or more acids and carbon dioxide. The grinding step can be carried out with any conventional grinding device such as a grinding mill known to the skilled person.

The surface-reacted natural or synthetic calcium carbonate to be used in the present invention may be in the form of a solid, but preferably is provided as an aqueous suspension having a pH, measured at 20° C., of greater than 6.0, preferably greater than 6.5, more preferably greater than 7.0, even more preferably greater than 7.5.

In a preferred process for the preparation of the aqueous suspension, the natural and synthetic calcium carbonate, either finely divided, such as by grinding, or not, is suspended in water. Preferably, the slurry has a content of natural or synthetic calcium carbonate within the range of 1 wt-% to 80 wt-%, more preferably 3 wt-% to 60 wt-%, and even more preferably 5 wt-% to 40 wt-%, based on the weight of the slurry.

In a next step, an acid, which, in the context of the present invention is a Brønsted acid, i.e. a $H_3O^+$ ion donor, is added to the aqueous suspension containing the natural or synthetic calcium carbonate. Preferably, the acid has a $pK_a$ at 25° C. of 2.5 or less. If the $pK_a$ at 25° C. is 0 or less, the acid is preferably selected from sulphuric acid, hydrochloric acid, or mixtures thereof. If the $pK_a$ at 25° C. is from 0 to 2.5, the acid is preferably selected from $H_2SO_3$, $M^+HSO_4^-$ ($M^+$ is an alkali metal ion selected from the group comprising sodium and potassium), $H_3PO_4$, oxalic acid or mixtures thereof.

The one or more acids can be added to the suspension as a concentrated solution or a more diluted solution. Preferably, the molar ratio of the acid to the natural or synthetic calcium carbonate is from 0.05 to 4, more preferably from 0.1 to 2.

As an alternative, it is also possible to add the acid to the water before the natural or synthetic calcium carbonate is suspended.

In a next step, the natural or synthetic calcium carbonate is treated with carbon dioxide. If a strong acid such as sulphuric acid or hydrochloric acid is used for the acid treatment of the natural or synthetic calcium carbonate, the carbon dioxide is automatically formed. Alternatively or additionally, the carbon dioxide can be supplied from an external source.

Acid treatment and treatment with carbon dioxide can be carried out simultaneously which is the case when a strong acid is used. It is also possible to carry out acid treatment first, e.g. with a medium strong acid having a $pK_a$ in the range of 0 to 2.5, followed by treatment with carbon dioxide supplied from an external source.

Preferably, the concentration of gaseous carbon dioxide in the suspension is, in terms of volume, such that the ratio (volume of suspension):(volume of gaseous $CO_2$) is from 1:0.05 to 1:20, even more preferably 1:0.05 to 1:5.

In a preferred embodiment, the acid treatment step and/or the carbon dioxide treatment step are repeated at least once, more preferably several times.

Subsequent to the acid treatment and carbon dioxide treatment, the pH of the aqueous suspension, measured at 20° C., naturally reaches a value of greater than 6.0, preferably greater than 6.5, more preferably greater than 7.0, even more preferably greater than 7.5, thereby preparing the surface-reacted natural or synthetic calcium carbonate as an aqueous suspension having a pH of greater than 6.0, preferably greater than 6.5, more preferably greater than 7.0, even more preferably greater than 7.5. If the aqueous suspension is allowed to reach equilibrium, the pH is greater than 7. A pH of greater than 6.0 can be adjusted without the addition of a base when stirring of the aqueous suspension is continued for a sufficient time period, preferably 1 hour to 10 hours, more preferably 1 to 5 hours.

Alternatively, prior to reaching equilibrium, which occurs at a pH greater than 7, the pH of the aqueous suspension may be increased to a value greater than 6 by adding a base subsequent to carbon dioxide treatment. Any conventional base such as sodium hydroxide or potassium hydroxide can be used.

Further details about the preparation of the surface-reacted natural calcium carbonate are disclosed in WO 00/39222, WO 2004/083316, WO 2005/121257, WO 2009/074492, EP 2 264 108 A1, EP 2 264 109 A1 and US 2004/0020410 A1, wherein the surface-reacted natural calcium carbonate is described as a filler for paper manufacture, the content of these references herewith being included in the present application.

Surface-reacted calcium carbonate being useful in the present invention may also be prepared by contacting ground natural calcium carbonate with at least one water-soluble acid and with gaseous $CO_2$, wherein said acid(s) have a $pK_a$ of greater than 2.5 and less than or equal to 7, when measured at 20° C., associated with the ionisation of their first available hydrogen, and a corresponding anion formed on loss of this first available hydrogen capable of forming water-soluble calcium salts. Subsequently, at least one water-soluble salt, which in the case of a hydrogen-containing salt has a $pK_a$ of greater than 7, when measured at 20° C., associated with the ionisation of the first available hydrogen, and the salt anion of which is capable of forming water-insoluble calcium salts, is additionally provided.

In this respect, exemplary acids are acetic acid, formic acid, propanoic acid and mixtures thereof, exemplary cations of said water-soluble salt are selected from the group consisting of potassium, sodium, lithium and mixtures thereof, and exemplary anions of said water-soluble salt are selected from the group consisting of phosphate, dihydrogen phosphate, monohydrogen phosphate, oxalate, silicate, mixtures thereof and hydrates thereof.

Further details about the preparation of these surface-reacted natural calcium carbonates are disclosed in EP 2 264 108 A1 and EP 2 264 109 A1, the content of which herewith being included in the present application.

Similarly, surface-reacted precipitated calcium carbonate is obtained. As can be taken in detail from EP 2 070 991, surface-reacted precipitated calcium carbonate is obtained by contacting precipitated calcium carbonate with $H_3O^+$ ions and with anions being solubilized in an aqueous medium and being capable of forming water-insoluble calcium salts, in an aqueous medium to form a slurry of surface-reacted precipitated calcium carbonate, wherein said surface-reacted precipitated calcium carbonate comprises an insoluble, at least partially crystalline calcium salt of said anion formed on the surface of at least part of the precipitated calcium carbonate.

Said solubilized calcium ions correspond to an excess of solubilized calcium ions relative to the solubilized calcium ions naturally generated on dissolution of precipitated calcium carbonate by $H_3O^+$ ions, where said $H_3O^+$ ions are provided solely in the form of a counterion to the anion, i.e. via the addition of the anion in the form of an acid or non-calcium acid salt, and in absence of any further calcium ion or calcium ion generating source.

Said excess solubilized calcium ions are preferably provided by the addition of a soluble neutral or acid calcium salt, or by the addition of an acid or a neutral or acid non-calcium salt which generates a soluble neutral or acid calcium salt in situ.

Said $H_3O^+$ ions may be provided by the addition of an acid or an acid salt of said anion, or the addition of an acid or an acid salt which simultaneously serves to provide all or part of said excess solubilized calcium ions.

In a preferred embodiment of the preparation of the surface-reacted natural or synthetic calcium carbonate, the natural or synthetic calcium carbonate is reacted with the acid and/or the carbon dioxide in the presence of at least one compound selected from the group consisting of silicate, silica, aluminium hydroxide, earth alkali aluminate such as sodium or potassium aluminate, magnesium oxide, or mixtures thereof. Preferably, the at least one silicate is selected from an aluminium silicate, a calcium silicate, or an earth alkali metal silicate. These components can be added to an aqueous suspension comprising the natural or synthetic calcium carbonate before adding the acid or carbon dioxide.

Alternatively, the silicate and/or silica and/or aluminium hydroxide and/or earth alkali aluminate and/or magnesium oxide component(s) can be added to the aqueous suspension of natural or synthetic calcium carbonate while the reaction of natural or synthetic calcium carbonate with an acid and carbon dioxide has already started. Further details about the preparation of the surface-reacted natural or synthetic calcium carbonate in the presence of at least one silicate and/or silica and/or aluminium hydroxide and/or earth alkali aluminate component(s) are disclosed in WO 2004/083316, the content of this reference herewith being included in the present application.

The surface-reacted natural or synthetic calcium carbonate can be kept in suspension, optionally further stabilised by a dispersant. Conventional dispersants known to the skilled person can be used. A preferred dispersant is polyacrylic acid.

Alternatively, the aqueous suspension described above can be dried, thereby obtaining the solid (i.e. dry or containing as little water that it is not in a fluid form) surface-reacted natural or synthetic calcium carbonate in the form of granules or a powder.

In a preferred embodiment, the surface-reacted natural or synthetic calcium carbonate has a specific surface area of from 5 $m^2/g$ to 200 $m^2/g$, more preferably 20 $m^2/g$ to 80 $m^2/g$ and even more preferably 30 $m^2/g$ to 60 $m^2/g$, measured using nitrogen and the BET method according to ISO 9277.

Furthermore, it is preferred that the surface-reacted natural or synthetic calcium carbonate has a weight median grain diameter of from 0.1 to 50 µm, more preferably from 0.5 to 25 µm, especially from 0.8 to 20 µm, most preferably from 1 to 10 µm, measured according to the sedimentation method. The sedimentation method is an analysis of sedimentation behaviour in a gravimetric field. The measurement of natural calcium carbonate is made with a Sedigraph™ 5100 of Micromeritics Instrument Corporation. The method and the instrument are known to the skilled person and are commonly used to determine grain size of fillers and pigments. The measurement is carried out in an aqueous solution of 0.1 wt-% $Na_4P_2O_7$. The samples were dispersed using a high speed stirrer and supersonicated.

The weight median grain diameter of the surface reacted calcium carbonate (MCC) was determined by using a Malvern Mastersizer 2000 Laser Diffraction System known to the skilled person.

In a preferred embodiment, the surface-reacted natural or synthetic calcium carbonate has a specific surface area within the range of 5 to 200 $m^2/g$ and a weight median grain diameter within the range of 0.1 to 50 µm. More preferably, the specific surface area is within the range of 20 to 80 $m^2/g$ and the weight median grain diameter is within the range of 0.5 to 25 µm. Even more preferably, the specific surface area is within the range of 30 to 60 $m^2/g$ and the weight median grain diameter is within the range of 0.7 to 7 µm.

The surface reacted calcium carrier is capable of associating and transporting an active agent. The association is based on the adsorption onto the surface of the surface-reacted calcium carbonate particles, be it the outer or the inner surface of the particles, as well as the ad- and/or absorption into the particle pores.

As mentioned above and in EP 2 168 572, it is believed that this intra- and inter-pore structure of the surface reacted calcium carbonate provides adsorption and/or absorption characteristics making them superior to common materials having similar specific surface areas.

Thus, the basic adsorption and/or absorption characteristics can be controlled by the pore size and/or pore volume and/or surface area for a given agent.

Preferably, the surface-reacted natural or synthetic calcium carbonate has an intra-particle porosity within the range of from 5 vol.-% (v/v) to 50 vol.-% (v/v), preferably of from 20 vol.-% (v/v) to 50 vol.-% (v/v), especially of from 30 vol.-% (v/v) to 50 vol.-% (v/v) calculated from a mercury porosimetry measurement.

From the bimodal derivative pore size distribution curve the lowest point between the peaks indicates the diameter where the intra and inter-particle pore volumes can be separated. The pore volume at diameters greater than this diameter is the pore volume associated with the inter-particle pores. The total pore volume minus this inter particle pore volume gives the intra particle pore volume from which the intra particle porosity can be calculated, preferably as a fraction of the solid material volume, as described in *Transport in Porous Media* (2006) 63: 239-259.

Thus, the inter-particle porosity determined as the pore volume per unit particle volume is within the range of from 20 vol.-% (v/v) to 99 vol.-% (v/v), preferably from 30 vol.-% (v/v) to 70 vol.-% (v/v), more preferably from 40 vol.-% (v/v) to 60 vol.-% (v/v), e.g. 50 vol.-% (v/v), calculated from a mercury porosimetry measurement.

As already mentioned adsorption and/or absorption and release of the active agent is essentially controlled by the pore size, which preferably is in a range of from 10 to 100 nm, more preferably in a range of between 20 and 80 nm, especially from 30 to 70 nm, e.g. 50 nm determined by mercury porosimetry measurement.

Thus, generally, any agent fitting into the intra- and/or inter particle pores of the surface-reacted calcium carbonate carrier is suitable to be transported by the surface-reacted calcium carbonate carriers according to the invention.

Within these ranges any active agent, be it in industrial, agricultural or any other applications, such as for the transport in or into the human or animal body, can be useful in the present invention, e.g. agents selected from the group comprising antimicrobially, pharmaceutically, biologically, cosmetically active agents, nutrients, e.g. vitamines, salts, boosters such as caffeine and guarana, as well as health-promoting bacteria such as probiotics, scented agents or flavoring agents, biocides, fungicides, pesticides or herbicides, and disinfecting agents.

Especially preferred are active agents from the group of active agents mentioned in the Biocidal Products Directive 98/8/EC (BPD), preferably Product Type (PT) 1-23, more preferably PT6 and 12, most preferably PT6-13.

For example, active agents such as those selected from the group comprising glutardialdehyde (GDA), isothiazlinones such as 2-methyl-2H-isothiazol-3-one (MIT), 5-chloro-2-methyl-2H-isothiazol-3-one (CMIT), benzisothiazolinone (BIT), octyl-isothiazolinone (OIT), 4,5-dichloro-2-n-octyl-4-isothiazol-3-one (DCOIT), 2-bromo-2-nitro-1,3-propandiol (Bronopol), 2,2-dibromo-3-nitrilopropionamide (DBNPA), o-phenylphenol (OPP) and it salts, phenoxyethanol, formaldehyde, ethyleneglycolhemiformals, 1-(3-chloroallyl)-3,5,7-Triaza-1-azoniaadamantane chloride, tetrakishydroxymethyl phosphonium sulfate (THPS), 4,4-dimethyloxazolidine (DMO), hexahydro-1,3,5-tris(2-hydroxyethyl)-s-triazine, hexahydro-1,3,5-triethyl-s-triazine (HTT), tetrahydro-3,5-dimethyl-2H-1,3,5-thiadiazine-2-thione (DAZOMET), 3-iodo-2-propynyl butyl carbamate (IPBC), 5-chloro-2-(2,4-dichlorophenoxy)-phenol (triclosan); and derivatives, salts and mixtures thereof; anticarcinogens, limonene, peppermint, surfactants like defoamers, or softeners, mineral oils, silicon, wetting agents, wax, paraffin, hydrolytic agents such as hydrolytic binders, and antidusting oils can be used.

In preferred embodiments glutardialdehyde, Bronopol, isothiazolinones such a MIT, CMIT, BIT, OIT, and mixtures thereof are used.

For example, a mixture of glutardialdehyde and CMIT/MIT in a weight ratio of about 23.5:1.05:0.35 may be used.

In a preferred embodiment of the invention, the core comprising the surface-reacted calcium carbonate and at least one active agent is in the form of tablets, pellets, granules, or powder.

As mentioned above, it has turned out that by combining a core of surface-reacted calcium carbonate loaded with an active agent as described above with a coating significantly improves the carrier characteristics, e.g. in terms of protecting the active agent in detrimental environments, as well as with respect to the release characteristics and control.

Coating materials which may be advantageously used in the present invention are selected from water soluble polymers selected from the group comprising methyl cellulose, hydroxypropyl cellulose, hydroxypropylmethyl cellulose, hydroxyethyl cellulose, polyvinyl pyrrolidone, polyvinyl alcohol, sodium alginate, polyethylene glycol, pullulan, tragacanth gum, guar gum, acacia gum, arabic gum, polyacrylic acid, methylmethacrylate copolymer, carboxyvinyl polymer, amylose, high amylose starch, hydroxypropylated high amylose starch, dextrin, pectin, chitin, chitosan, gelatin, zein, gluten, soy protein isolate, whey protein isolate, casein, and derivatives, salts and mixtures thereof and from water-insoluble polymers selected from the group comprising hydrogenated vegetable oils, hydrogenated caster oil, polyvinyl chloride, shellac, polyurethane, cellulose derivatives, gum rosins, wood rosens, waxes, acrylate and methacrylate polymers, copolymers of acrylic and methacrylic acid esters, and derivatives, salts and mixtures thereof.

By a proper selection of an appropriate coating, the release and protection properties can be tailor-made depending on the active agent and the release environment.

For example, in a preferred embodiment of the invention, the protection and controlled release of heat sensitive antimicrobials can be appropriately controlled, e.g. by using a coating of methyl cellulose, which may be especially useful in industrial applications.

Thus, in an especially preferred embodiment, the coating material is methyl cellulose.

Furthermore, it is generally possible to combine the carriers according to the invention with other materials to form a suitable formulation for the respective application. They may e.g. be included in capsules, tablets, creams and the like. Also, it is possible to use the surface-reacted calcium carbonate suspended in water, oils such as mineral oil fractions or vegetable oils such as jojoba oil, or in alcohols such as ethyl alcohol.

It is however preferred that the carriers according to the invention are not used in formulations for the oral applications, especially oral applications, wherein the release of the active agent is essentially based on a mechanical release, such as in chewing gum formulations.

As can be seen from the above, the surface-reacted calcium carbonate carrier is useful to transport various agents associated therewith.

The loaded core may further comprise conventional galenical additives, such as lubricants, disintegrants, binders, antioxidants, pH adjusting agents, colorants, flavouring agents, stabilizers, etc., in conventional amounts.

For example, it might be useful to add 0.1 to 5 wt % based on the weight of the surface-reacted calcium carbonate, preferably 0.5 to 3 wt %, more preferably 1 to 2 wt % of a lubricant such as magnesium stearate.

In some embodiments, it is also advantageous to add disintegrants such as, e.g. sodium carboxymethyl cellulose, e.g. in amounts of from 0.5 to 10 wt % based on the weight of the surface-reacted calcium carbonate, preferably 3 to 8 wt %, more preferably 5 to 6 wt %.

The carriers according to the invention may be produced by a method comprising the following steps:
- providing the surface-reacted calcium carbonate,
- providing the active agent in the form of a solution or suspension in a suitable medium;
- contacting the surface-reacted calcium carbonate with the active agent,
- separating the loaded surface-reacted calcium carbonate from the excess liquid, solution or suspension,
- coating the separated loaded surface-reacted calcium carbonate with the coating material.

The association, i.e. adsorption and/or absorption of the agent onto and/or into the surface-reacted calcium carbonate carrier is generally effected by contacting the surface reacted calcium carbonate with a solution or suspension of the active agent in a suitable medium, which is preferably water, but can generally be any medium. However, if the medium is acidic, it needs to be weaker than the acid that formed the reacted surface salt and in dilute form. Then it can be exposed to a low pH for a limited time at least.

The surface-reacted calcium carbonate may be provided, e.g., be in the form of tablets, pellets, granules, or powder, which after the association step is separated from the excess liquid, solution or suspension, e.g. by filtration, and optionally dried.

It is also possible that the surface-reacted calcium carbonate is provided in powder form, contacted with the active agent, and subsequently, but before coating, brought into a certain form such as tablets, pellets, or granules using methods well-known in the art for this purpose.

Drying preferably is carried out by a well controllable drying method, such as gentle spray drying or oven-drying.

Subsequently, the core of surface-reacted calcium carbonate and at least one active agent associated therewith, is coated with coating material, by methods well known in the art, e.g. in a fluidized bed.

The resulting coated carrier may be applied directly or included in a formulation as described above, such as a cream, a tablet, capsule or any other formulation suitable for the respective application.

As already indicated above, the carrier according to the present invention has numerous advantages, and is especially useful for the transport of an active agent to a target environment, as well as for the controlled release of active agents.

It may be used in many fields such as in paper, paint, coating, pharmaceutical, biological, cosmetic, industrial, e.g. water purification, or agricultural applications.

However, it may be preferred that the use in formulations for oral applications, especially oral applications, wherein the release of the active agent is essentially based on a mechanical release, such as in chewing gum formulations is excluded.

The carrier may be especially useful in the transport and controlled release of heat sensitive active agents. A "heat sensitive" active agent in the context of the present invention means a compound which due to the exposure to heat either looses its activity or even is heat-degraded, thus chemically transformed.

Also, it has turned out that by selecting a suitable coating, the active agent may be not only well protected, e.g. from degrading due to excessive heat, but that it may even possible to have a temperature depending controlled release.

For example, the majority of industrially applied antimicrobials has a limited temperature stability, and degrades at temperatures of above 50° C.

A combination of surface-reacted calcium carbonate loaded with heat-sensitive active agents, e.g. antimicrobials such as glutardialdehyde, Bronopol, isothiazolinones such a MIT, CMIT, BIT, OIT, and mixtures thereof, and coated with methyl cellulose may prevent degradation of the active agent at temperatures up to 80° C.

Heat protection may generally be achieved up to 60° C., preferably up to 80° C., more preferably up to 100° C., most preferably up to 150° C.

It is advantageous according to the present invention, if the heat protection is effected at least some minutes such as 15 minutes or 30 minutes, up to hours such 2 to 12 hours, preferably up to 4 to 9 hours, e.g. 6 hours, and ideally up to 1 to 3 days, or even longer.

In the context of the present invention heat protection means that a heat-sensitive active agent still has its desired activity at the target environment after exposure to heat.

Thus, the use of surface-reacted calcium carbonate as an absorber and subsequent delivery vector for active agents, e.g. for antimicrobials, is beneficial for applications where a high load sustained "slow-release effect" is needed. By the combination with a coating, e.g. a methyl cellulose coating, it is possible to protect, e.g. heat-sensitive active agents, such as antimicrobials providing a controlled release of the actives at temperatures where they establish greatest persistence.

The industrial application of these findings contributes to a more efficient preservation with respect to both environmental as well as financial resources, and opens up a basis for alternative preservation strategies.

Thus, the present invention also relates to a method for transporting an active agent to a target environment and/or for the controlled release, preferably the temperature controlled release, of an active agent, preferably a heat sensitive active agent, as well as a method for protecting heat-sensitive active agents, using a carrier according to the invention, as defined above.

The following figures, examples and tests will illustrate the present invention, but are not intended to limit the invention in any way.

EXAMPLES

In order to evaluate the heat protection effect of the carriers according to the invention, two samples were prepared, a coated one and, for comparison reasons an uncoated one.

1. Measurement Methods

The following measurement methods were used to evaluate the parameters given in the examples and claims.

BET Specific Surface Area of a Material

The BET specific surface area was measured via the BET process according to ISO 9277 using nitrogen, following conditioning of the sample by heating at 250° C. for a period of 30 minutes. Prior to such measurements, the sample was filtered, rinsed and dried at 110° C. in an oven for at least 12 hours.

Particle Size Distribution (Mass % Particles with a Diameter<X) and Weight Median Diameter ($d_{50}$) of a Particulate Material:

Weight median grain diameter and grain diameter mass distribution of a particulate material were determined via the sedimentation process, i.e. an analysis of sedimentation behaviour in a gravitational field. The measurement was made with a Sedigraph™ 5100.

The weight median grain diameter of the surface reacted calcium carbonate was determined by using a Malvern Mastersizer 2000 Laser Diffraction System.

The processes and instruments are known to the skilled person and are commonly used to determine grain size of fillers and pigments. The measurements were carried out in an aqueous solution of 0.1 wt.-% $Na_4P_2O_7$. The samples were dispersed using a high speed stirrer and ultrasound.

HPLC Analyses

HPLC analyses were performed on a Waters 600 System with in-line degasser equipped with a 717 plus autosampler and a 2996 photodiode array detector (Waters AG, 5405 Baden-Dättwil, Switzerland). A Nucleosil 120-5 C18 column 250×4.6 mm of the company Macherey-Nagel (4702 Oensingen, Switzerland) was used.

HPLC Parameters:
Eluent: Water:Methanol; 70:30 v/v
Flow: 1 ml $min^{-1}$
Injection quantity: 10 µl
Wavelength: 275 nm
Temperature: 30° C.

2. Carrier Preparation

The pore structure of the surface reacted calcium carbonate was determined by mercury intrusion of the dry surface reacted calcium carbonate powder and compared with a compacted GCC sample (pellet) using a Micromeritics Autopore IV mercury porosimeter. The maximum pressure of mercury applied was 414 MPa, equivalent to a Laplace throat diameter of 4 nm. The mercury intrusion measurements have been corrected for the compression of mercury, expansion of the penetrometer and compressibility of the solid phase of the sample. This was performed using the software Pore-Cor (Gane, P. A. C., Kettle, J. P., Matthews, G. P. and Ridgway, C. J., (1996) Void Space Structure of Compressible Polymer Spheres and Consolidated Calcium Carbonate Paper-Coating Formulations, *Ind. Eng. Chem. Res.*, 35(5), 1753-1764; Pore-Cor is a software package of the Environmental and Fluid Modelling Group, University of Plymouth, PL4 8AA, UK).

Figure 1A:
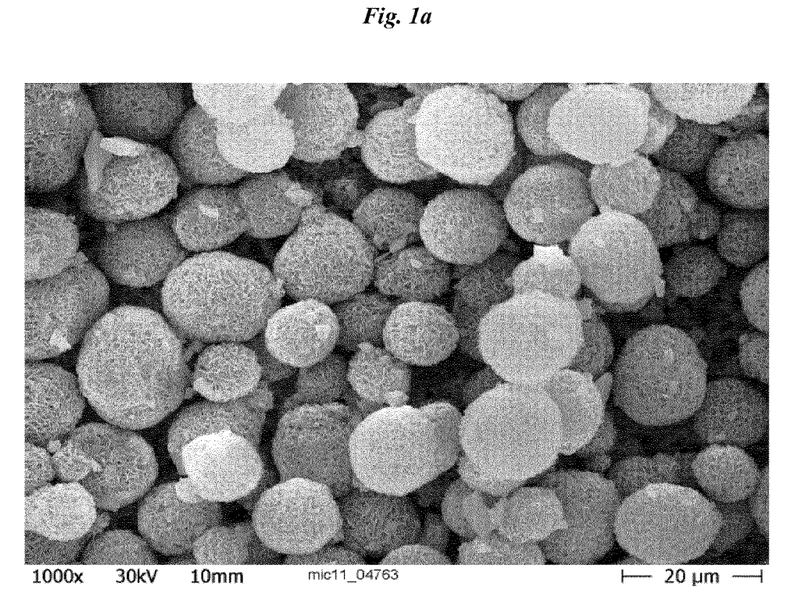
FIGS. 1a and 1b show SEM images of surface-reacted calcium carbonate (FIG. 1a) useful in the present invention and conventional GCC (FIG. 1b)
Figure 1B:
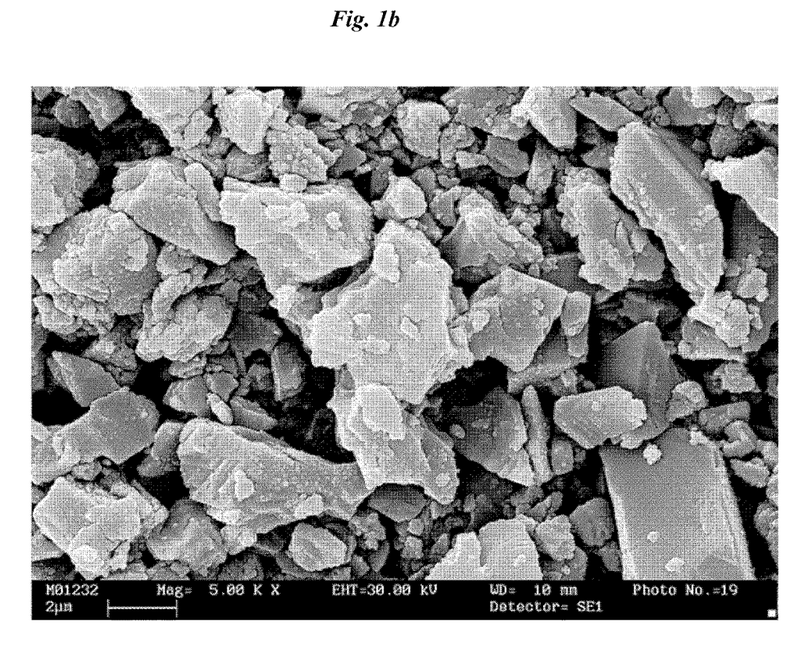
Figure 2A:
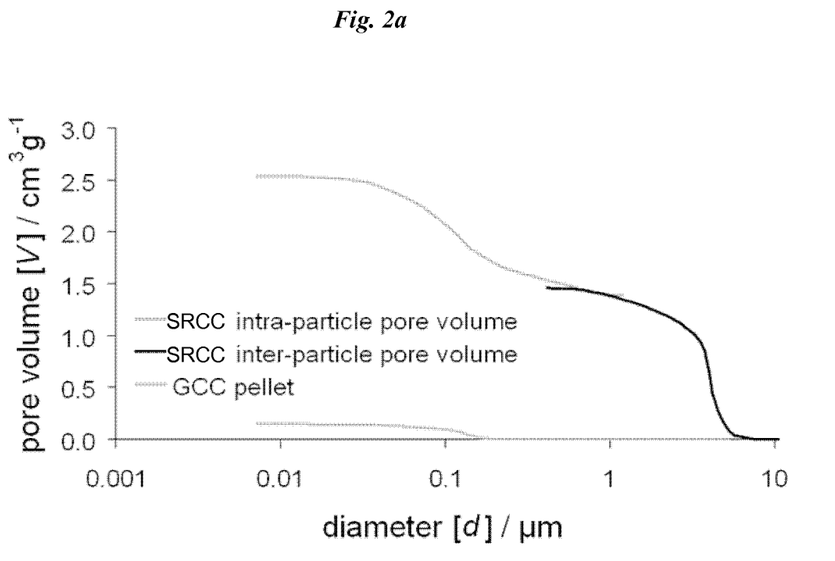
FIGS. 2a, b and c show graphs illustrating the porosity of surface reacted calcium carbonate (SRCC) according to the invention and known GCC, as well as their differential pore size distribution and their pore size distribution.
Figure 2B:
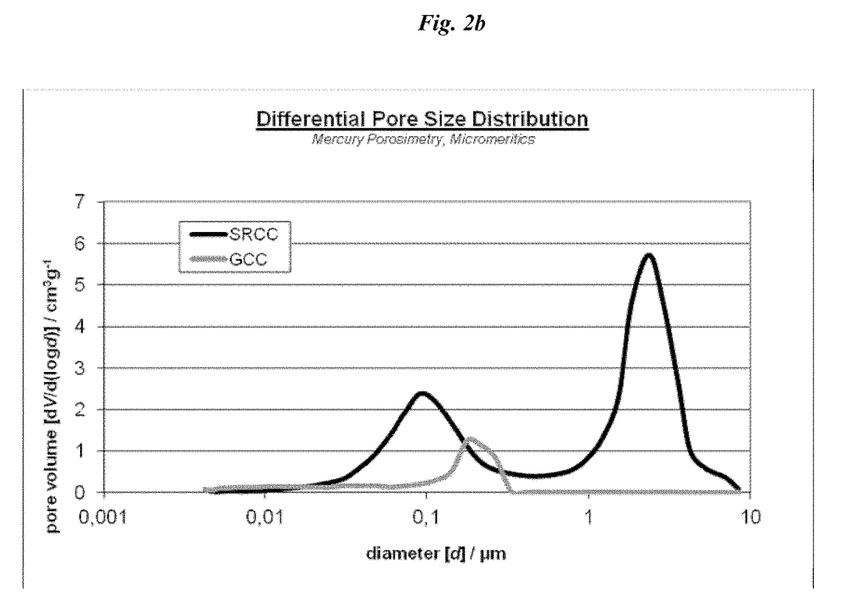
Figure 2C:
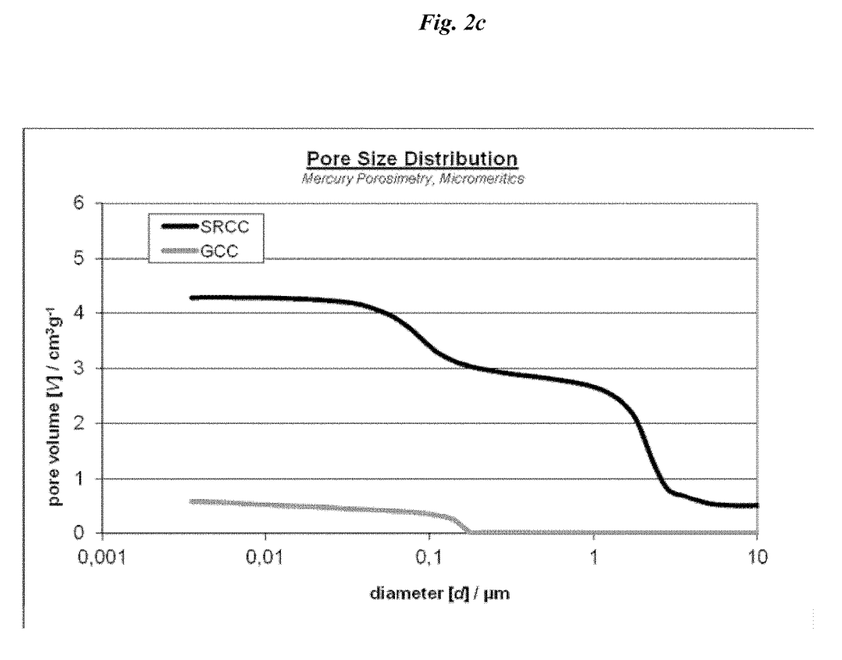

FIGS. 2a, b, and c illustrate the porosity of the surface reacted calcium carbonate (SRCC) used in the invention and known GCC, as well as their differential pore size distribution and their pore size distribution. The mercury intrusion curves of surface reacted calcium carbonate were divided into discretely bimodal inter- and intra-particle size regions. From these measurements a total porosity of 83 vol.-% (v/v), inter-particle porosity of 48 vol.-% (v/v), intra-particle porosity of 35 vol.-% (v/v) could be calculated, whereas compressed GCC only provided a pellet porosity of 29 vol.-% (v/v).

a) Formulation of Unloaded Surface-Reacted Calcium Carbonate Cores:

Surface-reacted calcium carbonate was well-mixed for about 30 minutes at room temperature with 1 wt % magnesium stearate (CAS No. 557-04-0) and 5 wt % sodium carboxymethyl cellulose (CAS No. 9004-32-4), based on the weight of the surface-reacted calcium carbonate, with a Turbula mixer, and subsequently pelletized using the eccentric press Korsch Pressen EKO (Korsch AG) using plungers having a diameter of 6 mm. The compression parameters were adjusted to a filling depth of 9 mm and a hardness of 6.

The quality of the resulting pellets was tested by a fracture strength test using a Pharma Test Typ PTB (Pharma Test Apparate Bau AG) and a disaggregation test. For testing disaggregation characteristics, the pelletized cores were dried at 150° C. to constant weight with the moisture analyzer MJ33 before taring. The disaggregation of a core was tested in 100 ml deionised water and Hydrocarb 90 for 30 minutes with stirring at 200 rpm. Capsule residues bigger than 45 µm were collected with a sieve, dried at 150° C. to constant weight and gravimetrically evaluated.

b) Association of Active Agent

The unloaded surface-reacted calcium carbonate cores subsequently were loaded with a 0.5 wt % solution of 2-methyl-2H-isothia-zol-3-one (MIT) in water (20 wt % MIT based on the weight of surface-reacted calcium carbonate) by pipetting it to 10 g of the cores of surface reacted calcium carbonate. For a homogenous distribution of the active agent the cores were mixed with a roll mixer for 2 days in a closed vessel.

c) Coating

For encapsulating the resulting loaded cores, Methocel A4M 4000 mPa·s (methyl cellulose available from Dow, CAS No. 9004-67-5) was used. Methyl cellulose swells quickly in cold water and can result in lumps. Therefore, a 2 wt % dispersion of methyl cellulose in hot water was prepared. The methyl cellulose dissolves during cooling down. The loaded cores of step b) were submerged for 15 minutes at 20° C. in 50 ml of the 2 wt % methyl cellulose dispersion and dried at room temperature for two days. The coating procedure was repeated three times.

3. Results

Release Behaviour

Figure 3:
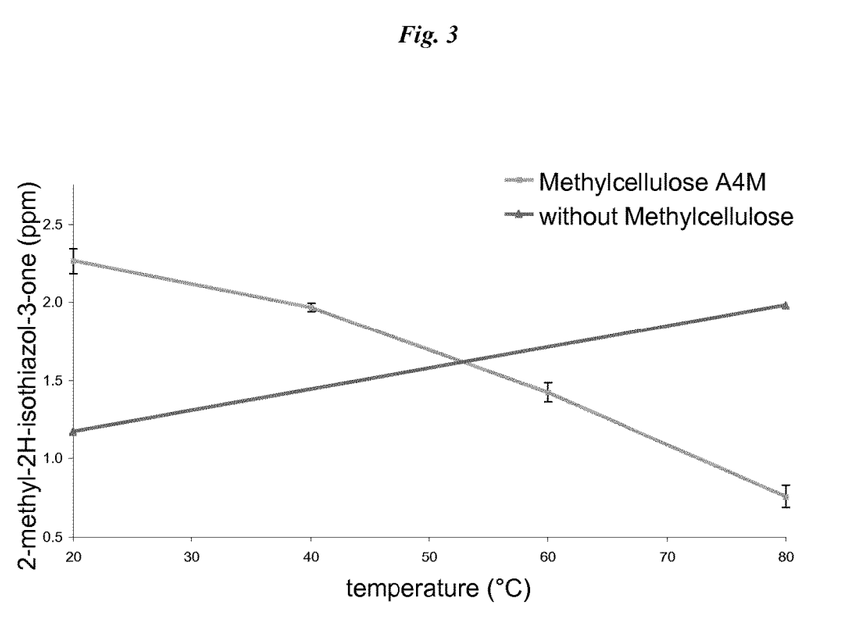
FIG. 3 shows a graph illustrating the release characteristics of coated and uncoated carriers after 4 h at different temperatures (in ppm).

FIG. 3 shows the temperature-dependent release rate of MIT from the cores being coated with methyl cellulose A4M and an uncoated core, respectively, as described above, after 4 hours at 80° C. and 20° C. in 100 ml deionised water determined by HPLC. It can clearly be seen that methyl cellulose was able to keep the MIT within the porous structure of the MCC at higher temperatures, whereas diffusion (release) can subsequently occur at lower temperatures.

The invention claimed is:

1. A carrier for the controlled release of an active agent at a target environment, comprising:
   a core, comprising
   surface-reacted natural or synthetic calcium carbonate having an inter-particle porosity of from 40 vol.-% (v/v) to 60 vol.-% (v/v), and an intra-particle porosity of from 30 vol.-% (v/v) to 50 vol.-% (v/v), calculated from a mercury porosimetry measurement,
   0.1 to 5 wt. % of a lubricant based on the weight of the surface-reacted calcium carbonate and/or 0.5 to 10 wt. % of a disintegrant based on the weight of the surface-reacted calcium carbonate, and
   at least one active agent,
   wherein a sufficient amount of the at least one active agent is adsorbed onto and/or absorbed into the natural or synthetic surface-reacted calcium carbonate, and
   wherein the surface-reacted natural or synthetic calcium carbonate is a reaction product of natural or synthetic calcium carbonate with carbon dioxide and one or more acids, wherein the carbon dioxide is formed in situ by the acid treatment and/or is supplied from an external source, and a coating encapsulating the core that is selected to protect the active agent and/or facilitate controlled release of the active agent in a target environment.

2. The carrier according to claim 1, wherein the surface-reacted natural or synthetic calcium carbonate is in the form of an aqueous suspension comprising the surface-reacted calcium carbonate and having a pH greater than 6.0 measured at 20° C.

3. The carrier according to claim 1, wherein natural calcium carbonate contains minerals selected from the group consisting of marble, calcite, chalk, dolomite, limestone and mixtures thereof.

4. The carrier according to claim 1, wherein synthetic calcium carbonate is precipitated calcium carbonate selected from the group consisting of aragonitic, vateritic and calcitic mineralogical crystal forms, and any mixture thereof.

5. The carrier according to claim 1, wherein the surface-reacted natural or synthetic calcium carbonate has a specific surface area of from 5 $m^2$/g to 200 $m^2$/g measured using nitrogen and the BET method according to ISO 9277.

6. The carrier according to claim 1, wherein the surface-reacted natural or synthetic calcium carbonate has a weight median grain diameter $d_{50}$ of from 0.1 to 50 μm measured according to the sedimentation method.

7. The carrier according to claim 1, wherein the at least one active agent is selected from the group consisting of an antimicrobial agent, a pharmaceutical agent, a biological agent, a cosmetically active agent, a nutrient, a vitamin, a salt, a booster, caffeine, guarana, a health-promoting bacteria, a probiotic, a scented agent, a flavoring agent, a biocide, a fungicide, a pesticide, a herbicide, and a disinfecting agent.

8. The carrier according to claim 1, wherein the at least one active agent is selected from the group consisting of glutardialdehyde (GDA), an isothiazlinone, 2-bromo-2-nitro-1,3-propandiol (Bronopol), 2,2-dibromo-3-nitrilopropionamide (DBNPA), o-phenylphenol (OPP) and a salt thereof, phenoxyethanol, formaldehyde, ethyleneglycolhemiformals, 1-(3-chloroallyl)-3,5,7-Triaza-1-azoniaadamantane chloride, tetrakishydroxymethyl phosphonium sulfate (THPS), 4,4-dimethyloxazolidine (DMO), hexahydro-1,3,5-tris(2-hydroxyethyl)-s-triazine, hexahydro-1,3,5-triethyl-s-triazine (HTT), tetrahydro-3,5-dimethyl-2H-1,3,5-thiadiazine-2-thione (DAZOMET), 3-iodo-2-propynyl butyl carbamate (IPBC), 5-chloro-2-(2,4-dichlorophenoxy)-phenol (triclosan); and a derivative, salt and mixture thereof an anticarcinogen, limonene, peppermint, a surfactant like defoamer, a softener, a mineral oil, silicon, a wetting agent, wax, paraffin, a hydrolytic agent, a hydrolytic binder, and an anti-dusting oil.

9. The carrier according to claim 1, wherein the at least one active agent is selected from the group consisting of 2-methyl-2H-isothiazol-3-one (MIT), 5-chloro-2-methyl-2H-isothiazol-3-one (CMIT), benzisothiazolinone (BIT), octyl-isothiazolinone (OIT), 4,5-dichloro-2-n-octyl-4-isothiazol-3-one (DCOIT), and a derivative thereof, a salt thereof, and any mixture thereof.

10. The carrier according to claim 1, wherein the core comprising a surface-reacted calcium carbonate and at least one active agent is in the form of a tablet, a pellet, granules, or powder.

11. The carrier according to claim 1, wherein the coating material is a water soluble polymer selected from the group consisting of methyl cellulose, hydroxypropyl cellulose, hydroxypropylmethyl cellulose, hydroxyethyl cellulose, polyvinyl pyrrolidone, polyvinyl alcohol, sodium alginate, polyethylene glycol, pullulan, tragacanth gum, guar gum, acacia gum, arabic gum, polyacrylic acid, methylmethacrylate copolymer, carboxyvinyl polymer, amylose, high amylose starch, hydroxypropylated high amylose starch, dextrin, pectin, chitin, chitosan, gelatin, zein, gluten, soy protein isolate, whey protein isolate, casein, and any mixture thereof.

12. The carrier according to claim 1, wherein the coating material is a water-insoluble polymer selected from the group consisting of a hydrogenated vegetable oil, hydrogenated caster oil, polyvinyl chloride, shellac, polyurethane, cellulose derivatives, a gum rosin, a wood rosin, a wax, an acrylate polymer, a methacrylate polymer, a copolymer of acrylic and methacrylic acid ester, and any mixture thereof.

13. The carrier according to claim 1 for the use in a paper, paint, coating, pharmaceutical, biological, cosmetic, or agricultural application.

14. The carrier according to claim 1 for transporting an active agent to a target environment.

15. The carrier according claim 1 for controlled release of an active agent.

16. The carrier according to claim 1, wherein the active agent is heat sensitive.

17. The carrier according to claim 1, wherein the controlled release is temperature controlled.

18. The carrier according to claim 1 for the protection of a heat-sensitive active agent.

19. A method for preparing a carrier according to claim 1 comprising the steps of
providing the surface-reacted calcium carbonate in admixture with the lubricant and/or the disintegrant,
providing the active agent in the form of a solution or suspension in a suitable medium;
contacting the surface-reacted calcium carbonate in admixture with the lubricant and/or the disintegrant with the active agent so that a sufficient amount of the active agent is adsorbed onto and/or absorbed into the surface-reacted calcium carbonate to obtain a loaded surface-reacted calcium carbonate,
separating the loaded surface-reacted calcium carbonate from the excess liquid, solution or suspension, and
coating the separated loaded surface-reacted calcium carbonate with a coating material that is selected to protect the active agent and/or facilitate controlled release of the active agent in a target environment.

20. A paper, paint, coating, pharmaceutical, biological, cosmetic, an industrial product or an agricultural product comprising the carrier according to claim 1.

21. A method for transporting an active agent to a target environment comprising introducing to the target environment the carrier according to claim 1.

22. The method according to claim 21, wherein the active agent is heat sensitive.

23. A method for the controlled release of an active agent comprising introducing the carrier according to claim 1 to a target environment and permitting the carrier to controllably release the active agent.

24. The method according to claim 23, wherein the controlled release is temperature controlled.

25. A method for protecting a heat-sensitive active agent comprising introducing the heat sensitive agent into the carrier according to claim 1.

* * * * *